US009198739B2

(12) United States Patent
Vu et al.

(10) Patent No.: US 9,198,739 B2
(45) Date of Patent: Dec. 1, 2015

(54) METHOD FOR PRODUCING A PATIENT-SPECIFIC BRACKET BODY AND CORRESPONDING BRACKET BODY

(75) Inventors: Hoang Viet-Ha Julius Vu, Unna (DE); Dirk Wiechmann, Bad Essen (DE)

(73) Assignee: DW Lingual Systems GmbH, Bad Essen (DE)

(*) Notice: Subject to any disclaimer, the term of this patent is extended or adjusted under 35 U.S.C. 154(b) by 0 days.

(21) Appl. No.: 13/984,467

(22) PCT Filed: Feb. 8, 2012

(86) PCT No.: PCT/EP2012/052143
§ 371 (c)(1),
(2), (4) Date: Aug. 8, 2013

(87) PCT Pub. No.: WO2012/116877
PCT Pub. Date: Sep. 7, 2012

(65) Prior Publication Data
US 2013/0313131 A1 Nov. 28, 2013

(30) Foreign Application Priority Data
Feb. 9, 2011 (DE) .......................... 10 2011 003 894

(51) Int. Cl.
*A61C 7/14* (2006.01)
*A61C 7/00* (2006.01)
*A61C 13/00* (2006.01)

(52) U.S. Cl.
CPC . *A61C 7/14* (2013.01); *A61C 7/002* (2013.01); *A61C 13/0004* (2013.01); *Y10T 29/49568* (2015.01)

(58) Field of Classification Search
CPC ...... A61C 7/14; A61C 13/0004; A61C 7/002; Y10T 29/49568

USPC ................ 29/896.1, 896.11; 433/8, 9, 10, 13
See application file for complete search history.

(56) References Cited

U.S. PATENT DOCUMENTS 4,193,195 A * 3/1980 Merkel et al. ................... 433/13
2002/0010568 A1   1/2002 Rubbert et al.
(Continued)

FOREIGN PATENT DOCUMENTS

CN      1372872 A    10/2002
DE      695 17 254   2/1996
(Continued)

OTHER PUBLICATIONS

International Preliminary Report on Patentability and Written Opinion, Aug. 22, 2013, Hoang Viet-Ha Julius Vu.

*Primary Examiner* — Ryan J Walters
(74) *Attorney, Agent, or Firm* — Greer, Burns & Crain, Ltd.

(57) ABSTRACT

Method for producing a patient-specific bracket body (7) for a modular bracket (1) having a pad (3) and a bracket body (7), which comprises the following steps:
 a) providing a raw bracket body (9) having a spacer section (9d),
 b) establishing a first parameter for cutting through the spacer section (9d), a distance of a resulting cut surface of the spacer section (9d) from the slot (11), in order to establish a suitable height of the bracket body (7),
 c) establishing a second parameter for cutting through the spacer section (9d), a cutting angle to a mesio-distal axis, in order to establish a suitable torque value of the bracket body (7),
 d) establishing a third parameter for cutting through the spacer section (9d), a cutting angle to an occlusal-gingival axis, in order to establish a suitable rotation value of the bracket body (7),
 e) cutting through the spacer section (9d) according to the three established parameters, whereby a bracket body (7) is produced.

9 Claims, 14 Drawing Sheets

(56) References Cited

U.S. PATENT DOCUMENTS

Figure 1:
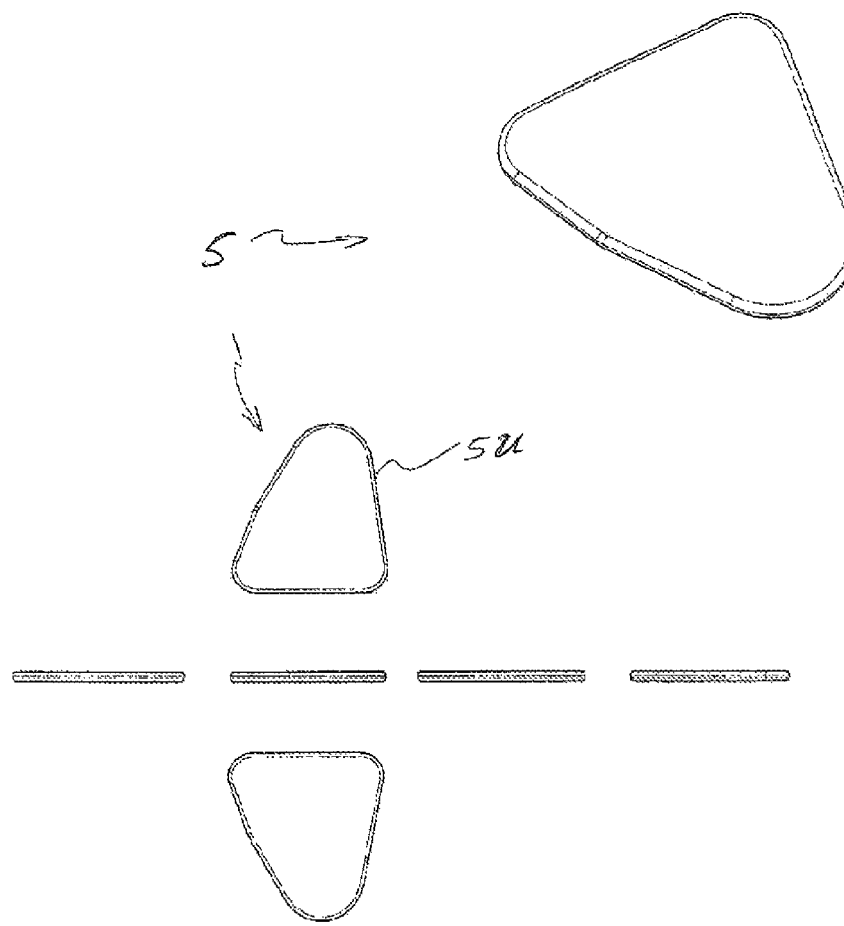

| | | |
|---|---|---|
| 2002/0119414 A1 | 8/2002 | Orikasa |
| 2004/0175669 A1 | 9/2004 | Abels et al. |
| 2007/0128571 A1 | 6/2007 | Kimura |
| 2010/0003632 A1* | 1/2010 | Ruiz Diaz et al. .............. 433/11 |
| 2010/0324715 A1 | 12/2010 | Yang et al. |

FOREIGN PATENT DOCUMENTS

| | | |
|---|---|---|
| DE | 11 2008 003 730 | 3/2011 |
| EP | 1080697 A1 | 2/1999 |
| EP | 0 695 539 | 5/2000 |
| EP | 1 844 730 | 10/2007 |
| EP | 1 941 842 | 7/2008 |
| EP | 1 474 064 | 11/2008 |
| EP | 1 702 582 | 10/2010 |
| JP | H11501832 A | 2/1999 |
| JP | H11226033 A | 8/1999 |
| JP | 2005516727 A | 6/2005 |
| JP | 3779984 B1 | 3/2006 |
| JP | 2011004833 A | 1/2011 |
| WO | 9628111 A1 | 1/1996 |
| WO | WO 03/092529 | 11/2003 |

* cited by examiner for tooth 23 for tooth 27 for tooth 35

Fig. 11

| | | | | | | | | | | | | | | | | | | | | | |
|---|---|---|---|---|---|---|---|---|---|---|---|---|---|---|---|---|---|---|---|---|---|
|UJ_FGZ|18|17|16|15|14| | | | | | | | | | | | | | | |28|
|UJ_OKZ|18|17|16|15|14|13|12|11| |21|22|23|24|25| |27|27| | | | |28|
|UJ_KZ|18|17|16|15|14|13|12|11|21|22|23|24|25|26|27|28| | | | | | |
|UJ_GZ|18|17|16|15|14|13|12|11|21|22|23|24|25|26|27|28| | | | | | |
|LJ_GZ|48|47|46|45|44|43|42|41|31|32|33|34|35|36|37|38| | | | | | |
|LJ_KZ|48|47|46|45|44|43|42|41|31|32|33|34|35|36|37|38| | | | | | |
|LJ_OKZ|48|47| |45|44| | | | | | |34|35| |37|38| | | | | | |
|LJ_FGZ|48|47|46|45|44| | | | | | |34|35|36|37|38| | | | | | |

METHOD FOR PRODUCING A PATIENT-SPECIFIC BRACKET BODY AND CORRESPONDING BRACKET BODY

The invention concerns a method for producing a patient-specific bracket body and a corresponding bracket body.

For the orthodontic treatment of patients having fixed braces, brackets are glued on the teeth of the patient to be treated and connected to one another via an archwire, so that they form an arrangement of brackets with respectively a slot through which an archwire can be run. The brackets present a pad for connection with the tooth and a bracket body, which in particular receives the archwire in a slot.

Standard brackets can be used as brackets, which are normalised according to certain standard values and may hence be used for a certain range of patients. There is also the possibility to have brackets manufactured individually for patients as disclosed for instance in EP1474064B1, EP07111572A1, U.S. 20020010568A1 and EP08103240.

While the manufacture of standard brackets does not raise any problems, the production of completely individualised brackets is quite wasteful. In a variation, individual bracket components such as for instance a hook, a wing, a slot for receiving an arch wire and a pad for setting up on a tooth are available in a computer, which are then assembled to build a virtual bracket, whereas this takes place in a virtual set-up of a patient's denture. The virtual bracket so obtained is transferred to a 3D printer to manufacture a real bracket therewith.

The standard brackets have been perceived as detrimental inasmuch as they do not allow for individualisation for a given patient. The wasteful production has been perceived as detrimental with completely individualised brackets.

The object of the present invention is hence to manufacture a patient-specific bracket body in a simple way and preferably a patient-specific bracket with such a bracket body.

This object is satisfied by a method having the characteristics of the claims and a bracket body manufactured according to the method.

GENERAL DESCRIPTION OF THE INVENTION

In particular, the bracket body is formed with the following method steps:

a) providing of a raw bracket body, which exhibits a spacer section, b) establishing a first parameter for cutting through the spacer section (9d), wherein the first parameter establishes a distance of the resulting cut surface of the spacer section from the slot, in order to establish a suitable height of the bracket body, c) establishing a second parameter for cutting through the spacer section (9d), wherein the second parameter establishes a cutting angle with respect to the mesio-distal axis, in order to establish a suitable torque value of the bracket body, d) establishing a third parameter for cutting through the spacer section (9d), wherein the third parameter establishes a cutting angle with respect to the occlusal-gingival axis, in order to establish a suitable rotation value of the bracket body, e) cutting through the spacer section according to the three established parameters. For the production of a bracket, the cut surface is connected to a pad which in particular comprises a constant thickness between two plane surfaces.

The raw bracket body is advantageously manufactured in step a) by a MIM or selective laser melting process, wherein it is advantageously generated or produced from a biocompatible metal or a biocompatible alloy, in particular titanium, gold, silver, stainless steel or a cobalt-chrome alloy.

The cutting through in step e) takes place preferably using a saw.

In a variation, that the parameters are established in steps b) to d) individually for a given patient.

In another variation, the parameters in steps b) to d) are respectively varied in a preset interval with preset interval steps, to generate a bracket body library in which bracket bodies are arranged with the respective different parameter values.

To produce a bracket, a pad for connection with a bracket body is prepared for every tooth of a patient to be treated.

Every pad is subsequently connected with a bracket body, in particular by gluing or welding, to produce a bracket for every tooth of a patient to be treated.

The brackets subsequently are respectively positioned in a malocclusion model of the patient on the matching tooth to be treated and a transfer tray is then obtained. Preferably, the brackets are arranged with their pad on a tooth surface, on the malocclusion model which shows the dentition out of position and a mass is arranged against the brackets, which fixes the brackets in their respective position, which they occupy on a tooth of said dentition.

According to the method previously described, bracket bodies as well as brackets, which include a bracket body connected to a pad, can be individualised specific for the patient.

A bracket body library of raw bracket bodies is preferably produced with bracket body containers for accommodating bracket bodies, wherein the bracket body containers are arranged in a matrix pattern. Bracket bodies are arranged in the bracket body containers. The bracket bodies are advantageously arranged in the bracket body containers, sorted line-by-line according to a parameter and column-by-column according to another parameter. Both parameters are preferably varied respectively within selected interval limits with selected interval steps. Advantageously, one of the parameters is the third or the second parameter and the other parameter is the second or the third parameter.

The bracket body comprises a cut surface spaced apart by a spacer section, which is obtained by cutting through, in particular sawing. The spacer section spaces the cut surface apart from the slot of the bracket body and has a length which as a first parameter establishes a suitable height of the bracket body. The cut surface is allocated to the mesio-distal axis as a second parameter in a cutting angle and establishes a suitable torque value of the bracket body. Additionally, the cut surface is allocated to the occlusal-gingival axis as the third parameter in a cutting angle, which establishes a suitable rotation value of the bracket body. The cut surface is hence established by the three parameters. The connection of the cut surface of the spacer section of the bracket body with the pad, which in particular presents a flat surface, preferably a constant material thickness establishes the arrangement of the bracket body with respect to the pad using the three parameters, and hence establishes the arrangement of the slot in the bracket body, adapted for the three parameters on the pad.

DETAILED DESCRIPTION OF THE INVENTION

Figure 2:
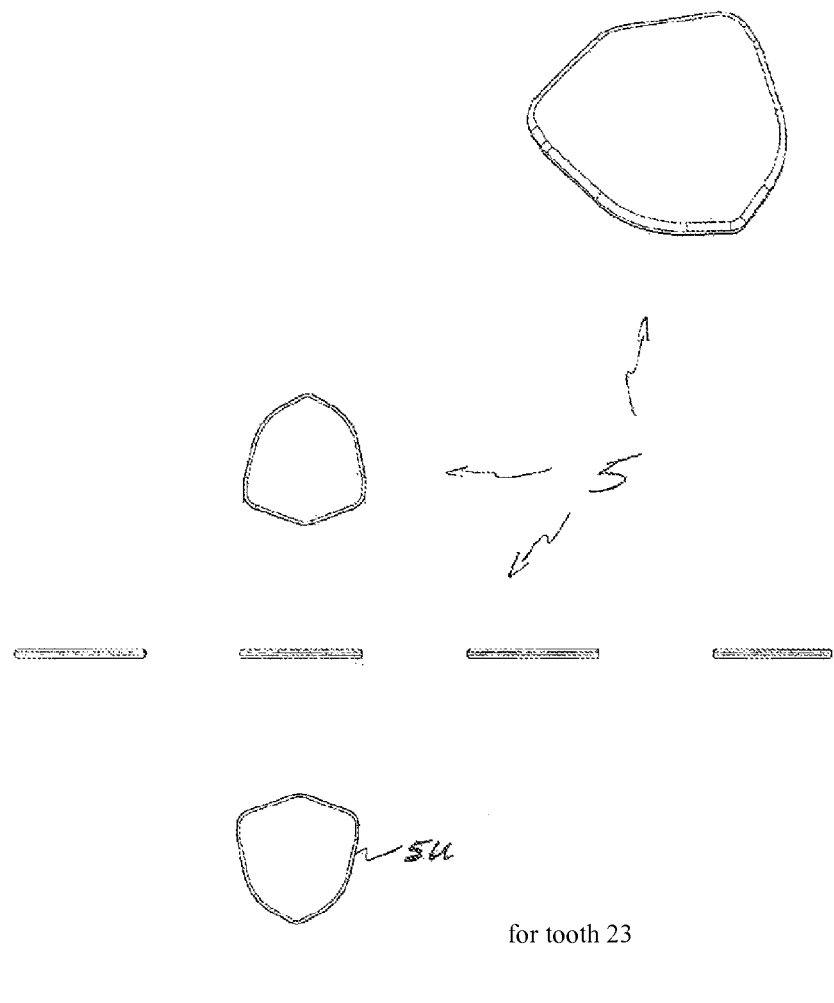
Figure 3:
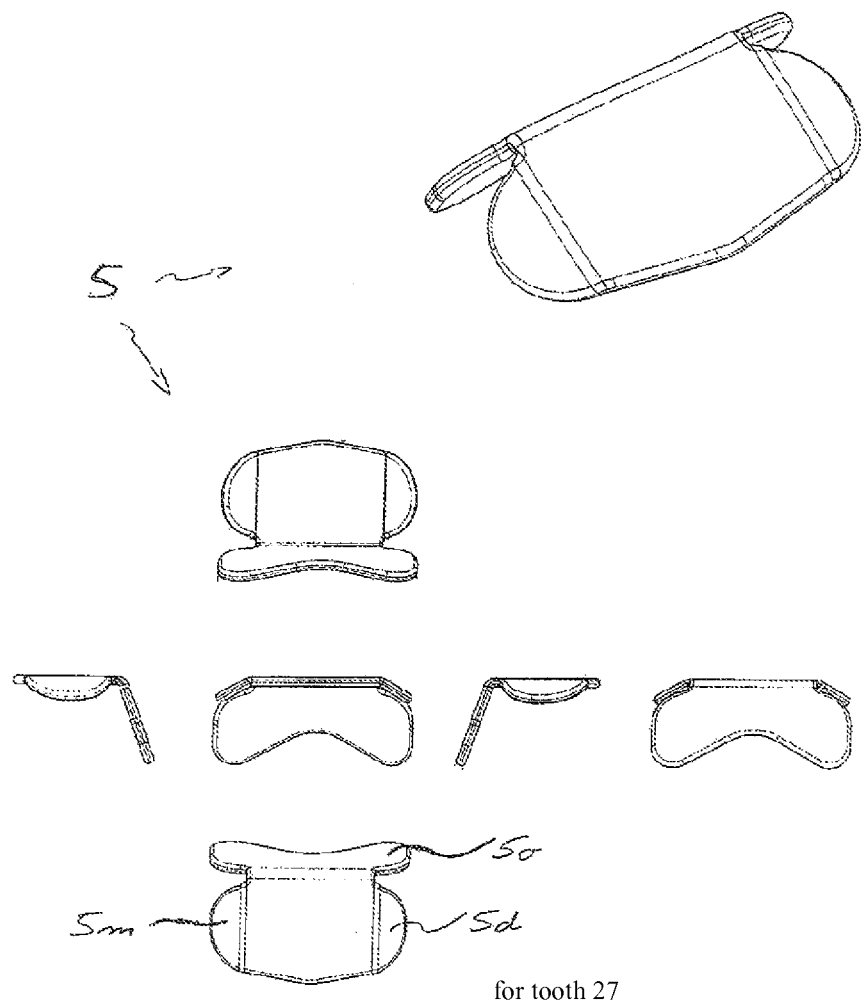
Figure 4:
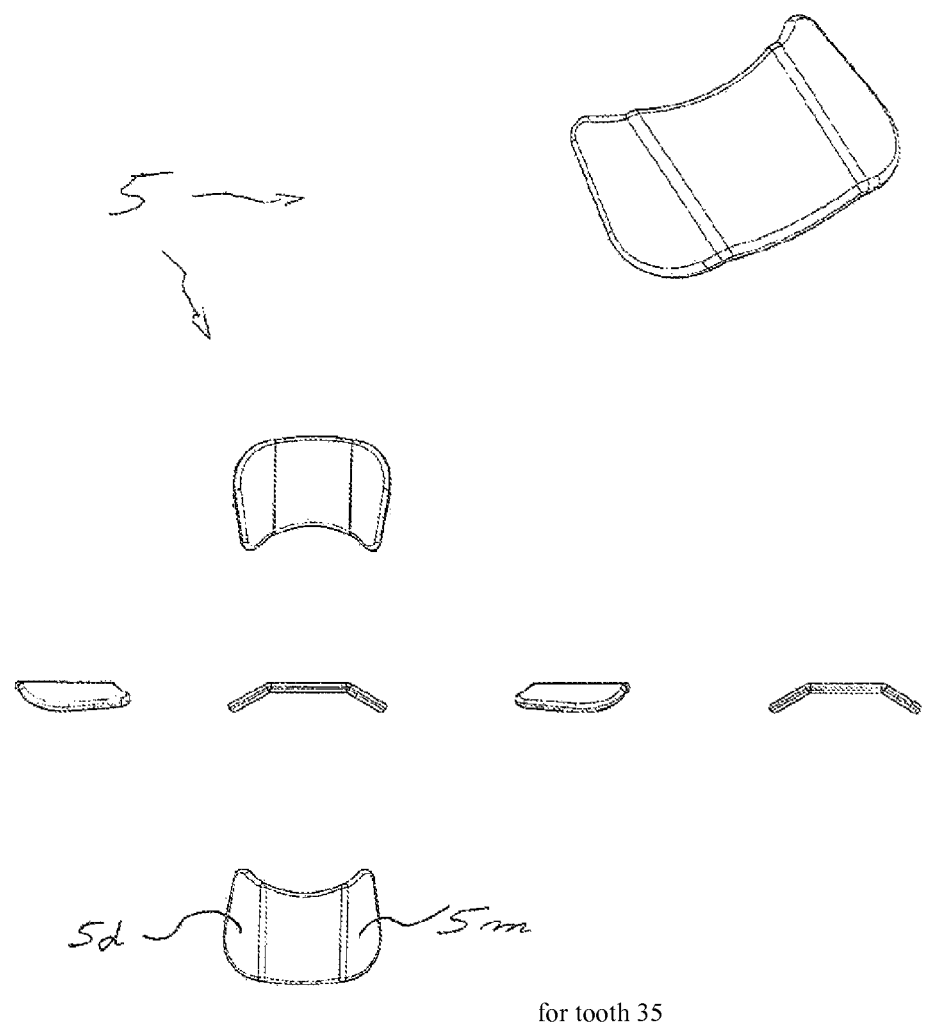
Figure 5:
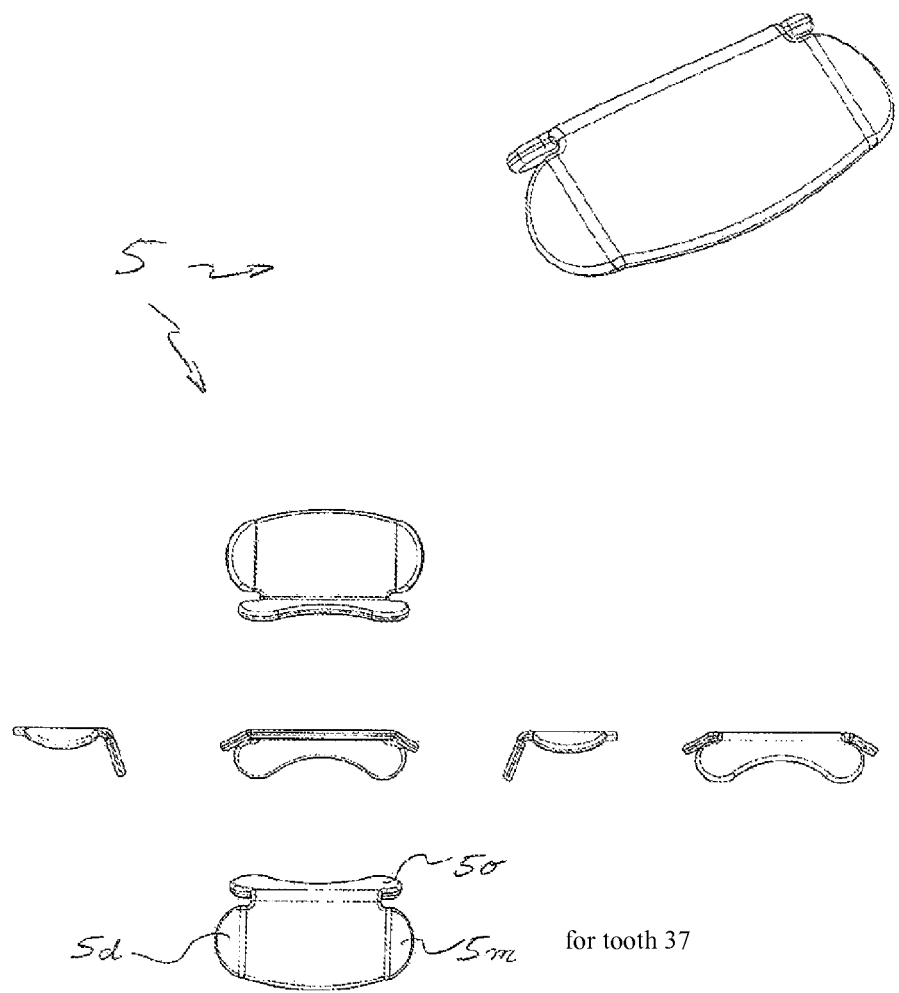
Figure 6:
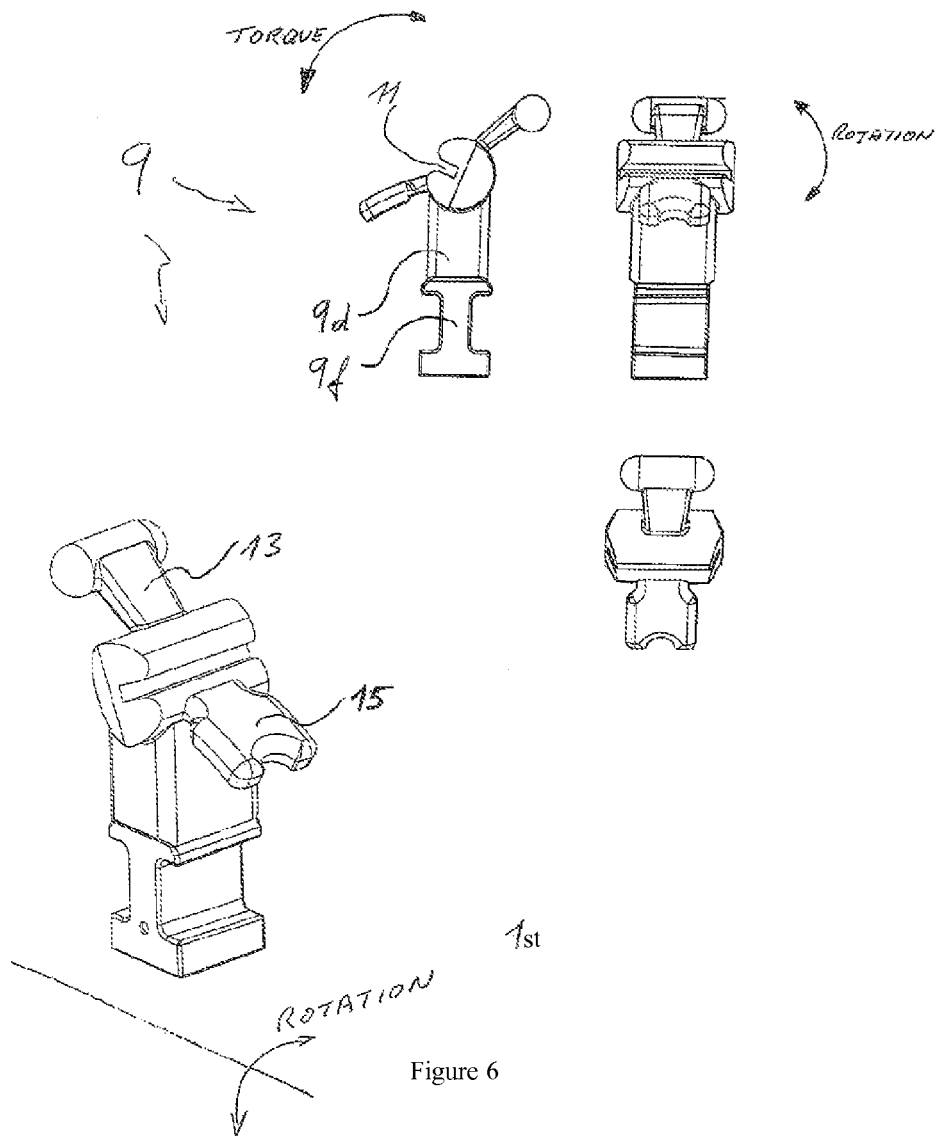
Figure 6A:
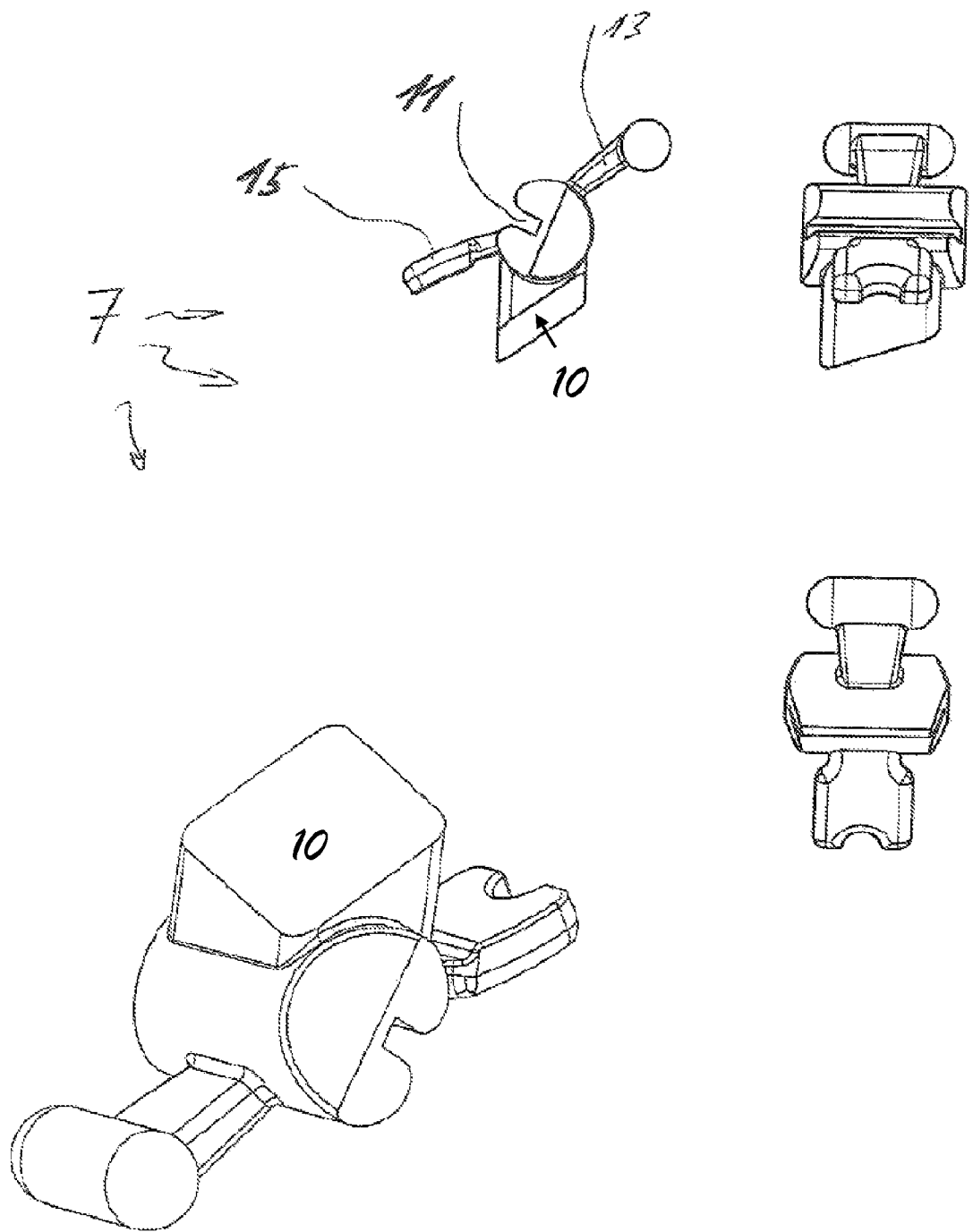
Figure 7:
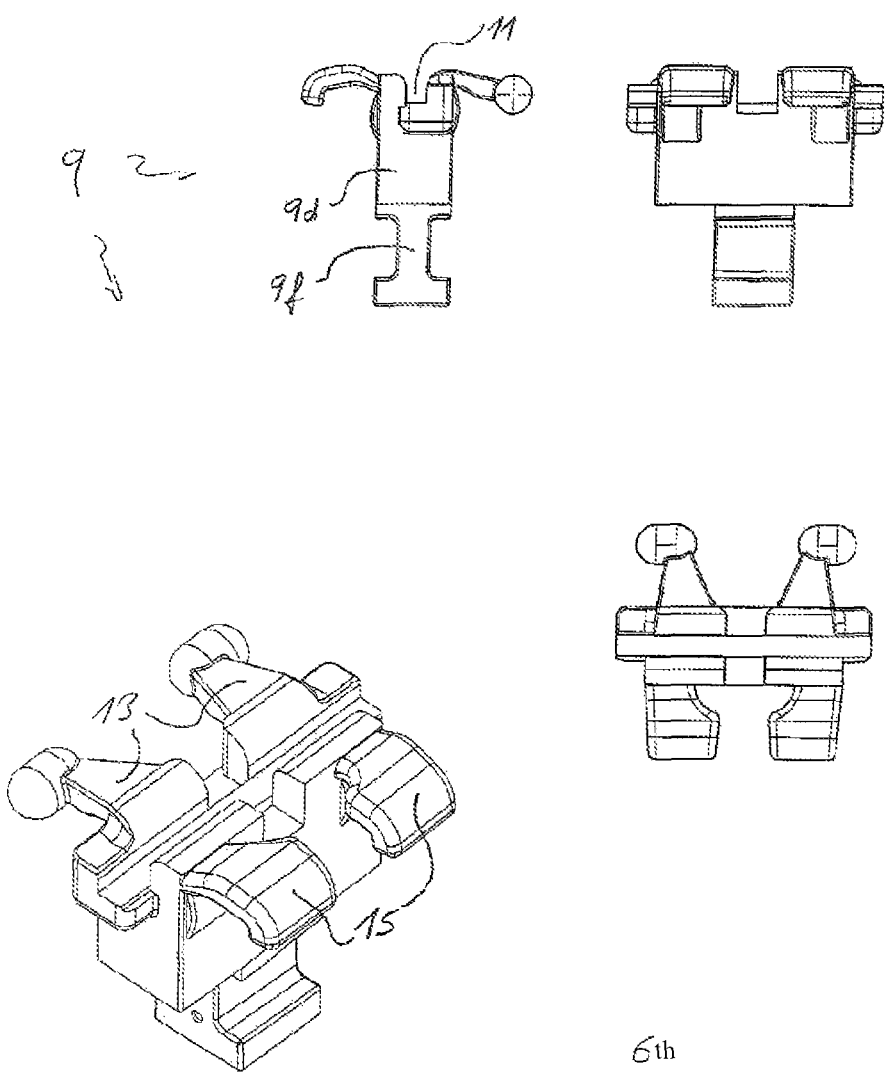
Figure 8:
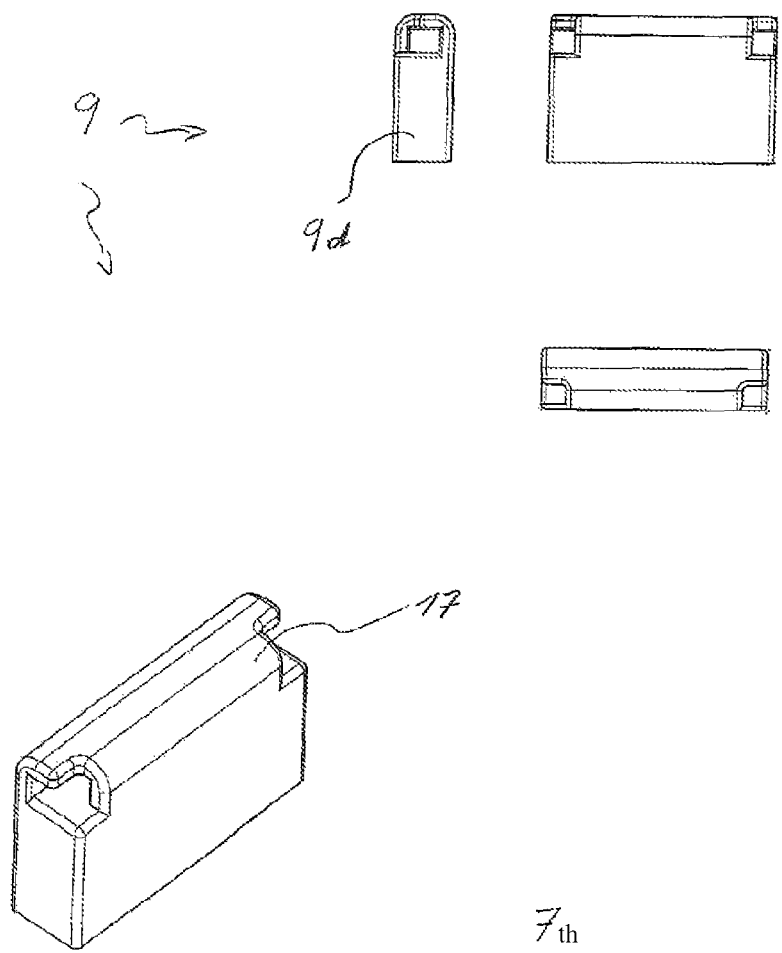
Figure 8A:
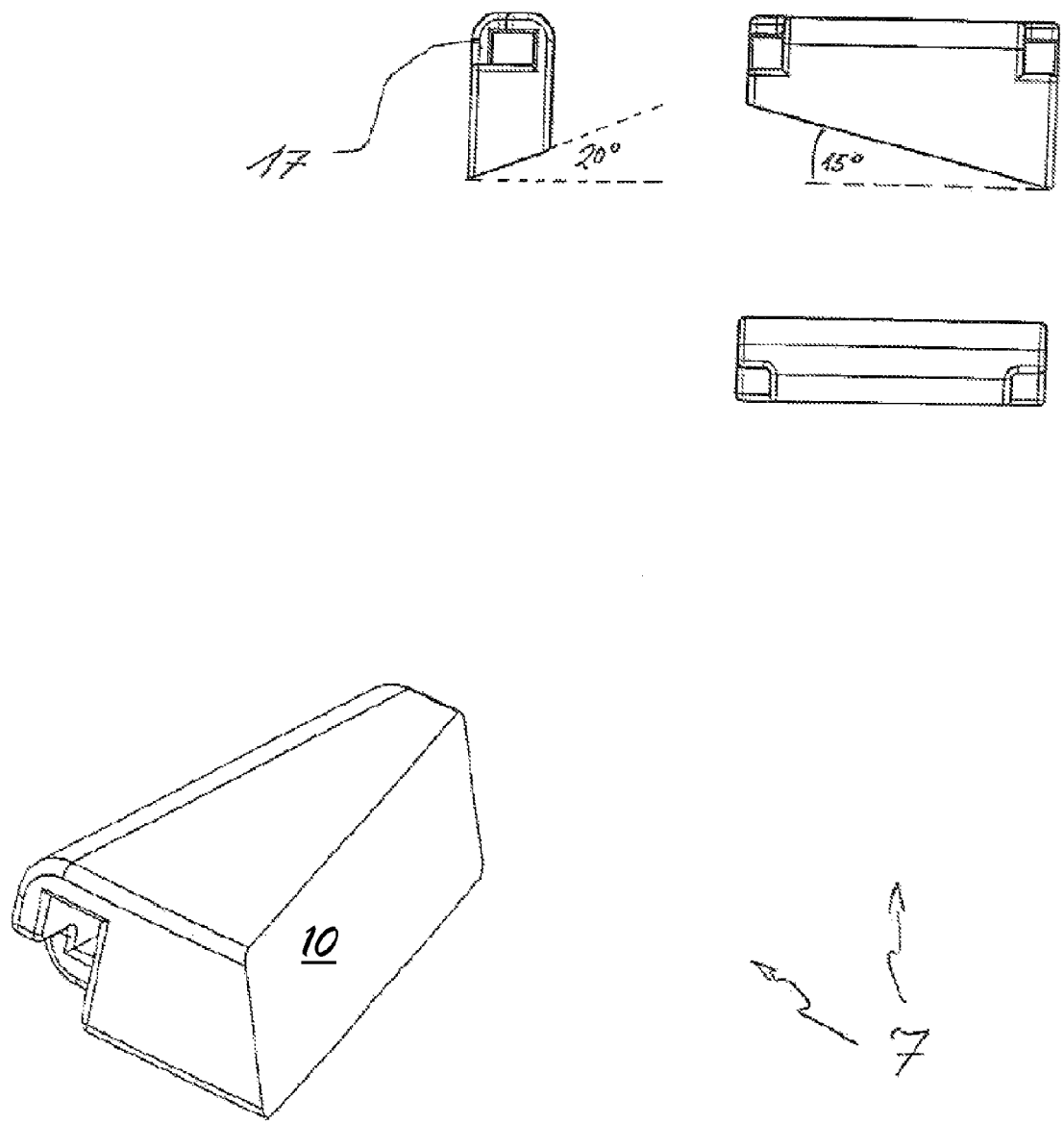
Figure 9:
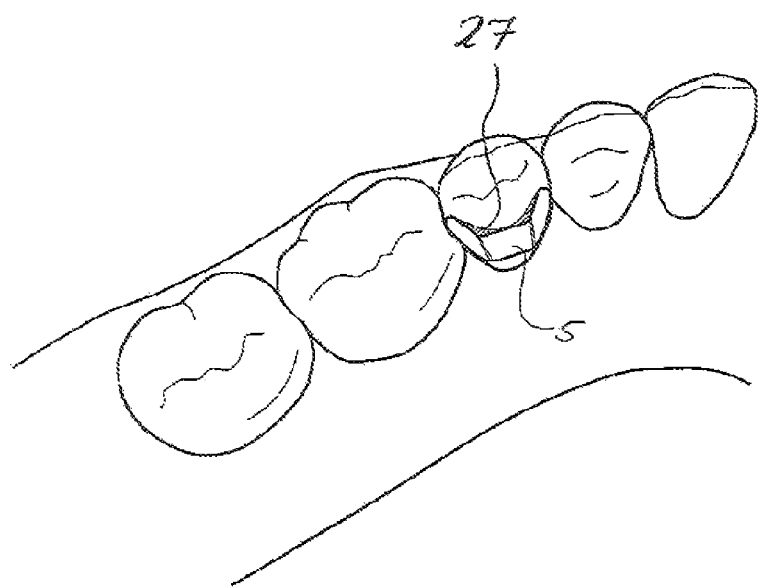
Figure 10:
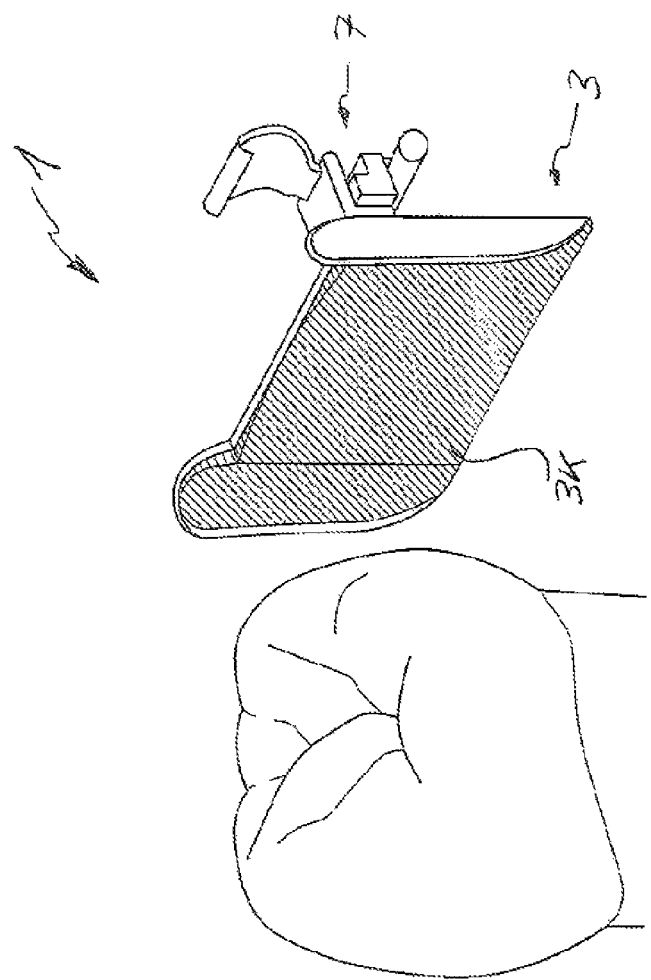
Figure 12:
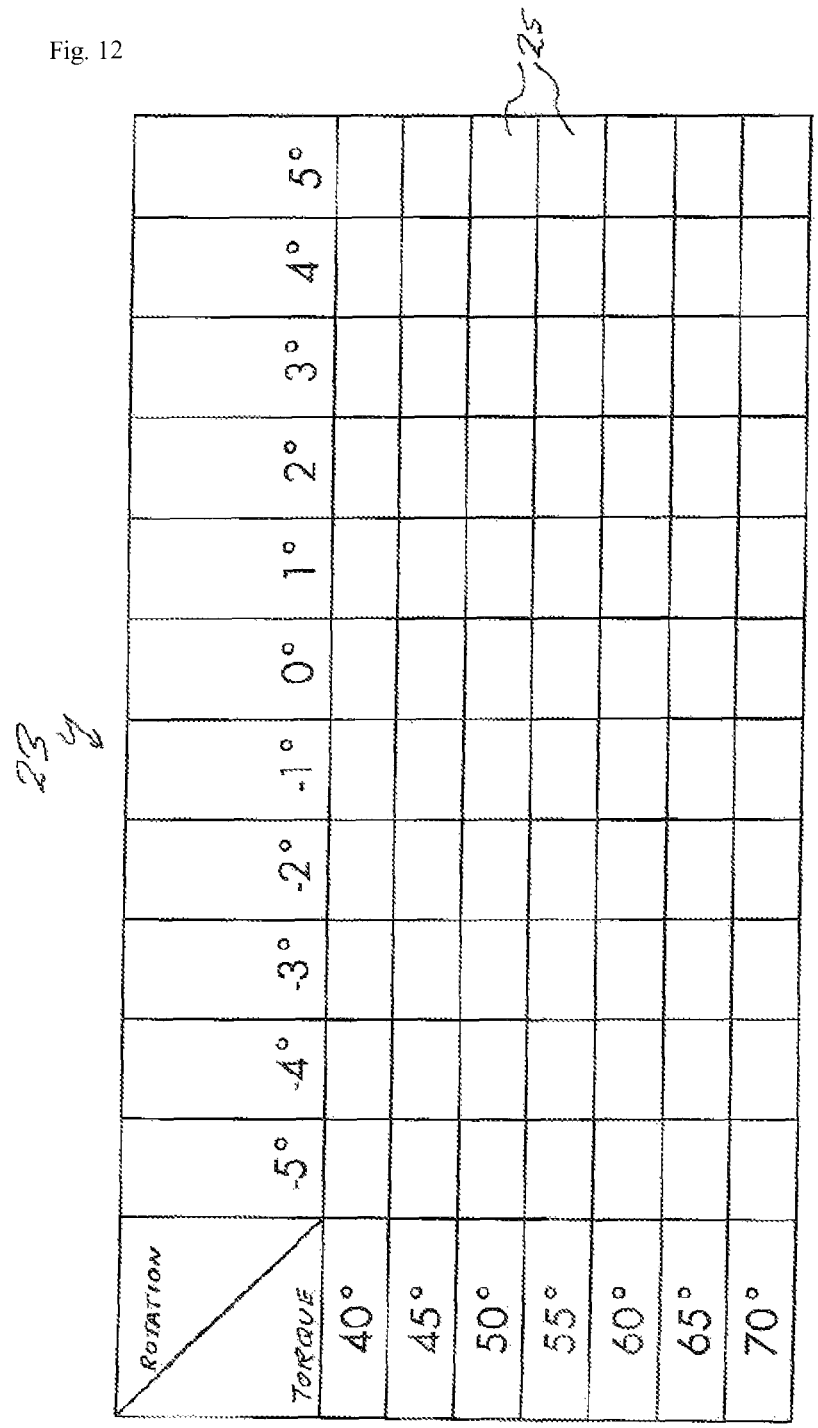

Additional characteristics, details and advantages of the invention can be seen in the claims and the following description of preferred embodiments as well as using the drawing. The figures are as follows:

FIG. 1 shows several views of a raw pad for the tooth 21,
FIG. 2 shows several views of a raw pad for the tooth 23,
FIG. 3 shows several views of a raw pad for the tooth 27,
FIG. 4 shows several views of a raw pad for the tooth 35, FIG. 5 shows several views of a raw pad for the tooth 37, FIG. 6 shows several views of a raw bracket body for the tooth 1 of the upper jaw (UJ 1st), FIG. 6a shows several views of a bracket body, produced from the raw bracket body of FIG. 6, FIG. 7 shows several views of a bracket body for the UJ or tooth 6 of the lower jaw (LJ 6th), FIG. 8 shows several views of a bracket body for the tooth 7 of the upper jaw (UJ) or lower jaw (LJ) (7th), FIG. 8a shows several views of a bracket body, produced from the raw bracket body of FIG. 8, FIG. 9 shows a perspective view of a target set-up, wherein a bracket body is arranged on a tooth and a gap between both is filled with plastic, FIG. 10 shows a perspective view of a tooth, on which a finished bracket is introduced, FIG. 11 is a top view on a raw pad library and FIG. 12 is a top view on a bracket body library.

First of all, there is provided a band of material for pads (100 m long, 5 cm wide and 0.4 mm thick) made of stainless steel as well as a punch with a punching stamp, to punch out raw pads out of the pad material band using the punch. The punch punches out several identical raw pads from an inlaid pad material section of the pad material band, wherein the buccal lingual perimeter of the same is adapted to the tooth for which the raw pad is produced. Instead of a pad material band, it is alternately possible also to use a sheet of pad material.

In FIG. 1 the six side views as well as a perspective view of a raw pad 5 for the tooth 21 are shown, which was produced that way. The raw pad 5 is flat and presents a constant material thickness over the whole surface. The buccal lingual perimeter 5U presents practically the form of a triangle which enables the raw pad 5 being adapted correctly to the tooth 21. The edges of the buccal lingual perimeter 5U, which were generated when punching out, were eliminated in a subsequent compression step, which produces the rounded lateral surfaces of said perimeter 5U.

Analogically, FIG. 2 shows a raw pad 5 produced according to the same method for the tooth 23, whereas said raw pad 5 differentiates itself from that of FIG. 1 exclusively through the other form of the buccal lingual perimeter 5U.

FIG. 3 shows the six side views as well as a perspective view of a raw pad 5 for the tooth 27. The raw pad 5 was produced following the same method, as described with reference to FIGS. 1 and 2, still two additional bending steps were however carried out. In a first bending step, a mesial 5m and a distal 5d wing section was formed by folding it over in a press with an appropriate bending tool. In a second bending step, an occlusal section 5o of the raw pad 5 was formed in a press with an appropriate bending tool. This occlusal section 5o rests occlusally on the tooth 27 in the status inserted in the patient.

FIG. 4 shows the six side views as well as a perspective view of a raw pad 5 for the tooth 35. The raw pad 5 was produced following the same method, as described with reference to FIGS. 1 and 2, a mesial 5m and a distal 5d wing section was however formed in a further bending step.

FIG. 5 shows the six side views as well as a perspective view of a raw pad 5 for the tooth 37. The raw pad 5 was produced following the same method, as described with reference to FIGS. 1 and 2, still two additional bending steps were however carried out, as described previously with reference to FIG. 3: In a first bending step, a mesial 5m and a distal 5d wing section was formed by folding it over in a press with an appropriate bending tool. In a second bending step, an occlusal section 5o of the raw pad 5 was formed in a press with an appropriate bending tool. This occlusal section 5o rests occlusally on the tooth 37 in the status inserted in the patient.

The raw pads 5 obtained that way were sorted into a raw pad library 19 which is represented on FIG. 11. The raw pad library 19 comprises 16 times 8 raw pad containers 21, which are arranged in a matrix pattern. In the row UJQZ and LJqz are respectively 16 raw pad containers 21, that is to say that a raw pad container 21 is provided for every tooth of the upper jaw and of the lower jaw. The raw pad containers 21 are arranged analogically to the FDI dental notation in the dentistry: from the tooth 8 (8th) left starting over the 1st to the right up to the 8th of the other half of the face. Accordingly, the raw pad containers are designated as 18 via 11 and 21 to 28, respectively as 48 via 41 and 31 to 38. The raw pad containers 5 belonging to the respective tooth are situated in each of said raw pad containers 21.

The row UJgz and LJaz contains the raw pads 5 for the upper jaw respectively the lower jaw with large teeth. The row UJkz and LJkz contains the raw pads 5 for the upper jaw respectively the lower jaw with large teeth. The row UJokz and LJokz contains the raw pads 5 with occlusal sections 5o for the upper jaw respectively the lower jaw with small teeth, in this instance only for the teeth 17, 18, 28, 27 as well as 34, 35, 37, 38, 44, 45, 47 and 48. The row ULfgz and LJfgz contains the raw pads 5 with wing sections 5m, 5d for the upper jaw respectively the lower jaw with big teeth, in this instance only for the teeth 14, 15, 16, 17, 18, 24, 25, 26, 27, 28 as well as 34, 35, 36, 37, 38, 44, 45, 46, 47 and 48.

To obtain now a patient-specific pad, the procedure is as follows: An impression of an upper jaw and lower jaw of a patient respectively is taken and a plaster model is prepared by using the former. The plaster models are mounted respectively arranged into an articulator which mirrors the relative position of the jaws relative to one another (malocclusion models). The target set-up is completed from said malocclusion model which depicts the planned situation at the end of the treatment. To prepare it, the teeth are cut out individually from the malocclusion models of the patient and then re-assembled in the target situation to reach, thereby producing the target set-up. A suitable raw pad 5 respectively for the teeth to be treated is taken from the raw pad library 19. The taken raw pads 5 are further adapted onto the corresponding teeth of the plaster model (target set-up) possibly by hand, wherein consequently the form and/or the size can be adapted, but bendings can still be carried out manually. Subsequently, the raw pads 5 are respectively held on the corresponding tooth in the target set-up and a gap 27 between the tooth and the raw pad 5 is filled with a filling material made of plastic, as shown in FIG. 9. In this manner, the raw pad 5 is given a patient-specific glued surface 3K and thus becomes a pad 3. This patient-specific glued surface 3K is in positive engagement with the tooth surface and can later be laid onto the tooth of the patient in a form locking manner and then be fixedly connected thereto using a glue.

The patient-specific pads 3 obtained that way are then only connected respectively to a patient-specific bracket body 7 which is taken from a bracket body library 23 which library is built analogically to the raw pad library, described as follows.

FIG. 6 shows different views of a raw bracket body 9 for an UJ 1st, wherein said presents a fixing section 9f, a spacer section 9d, a slot 11, a hook 13 and a wing 15. FIG. 6a shows the cut surface 10, which is arranged according to the three parameters.

FIG. 7 shows different views of a raw bracket body 9 for an UJ or a LJ 6th, wherein said presents a fixing section 9f, a spacer section 9d, a slot 11, two hooks 13 and two wings 15.

FIG. 8 shows different views of a raw bracket body 9 in the form of a little tube 17 for an UJ or a LJ 7th, wherein said also presents a spacer section 9d.

The raw bracket bodies 9 were produced in a metal injection moulding (MIM) process (alternately in a selective laser melting process) and consist of a cobalt-chrome alloy (alternately for instance made of stainless steel). The hooks 13 and wings 15 respectively present a material tapering on their end facing the slot 11, so that they can be bent respectively manually into a suitable angular position around the slot 11. To make an optimal slot 11 available for the treatment the raw bracket bodies 9 of the FIGS. 6 and 7 are fastened to a carrier with their fixing sections 9f. Approx. 100 pieces can be fixed to the carrier. The carrier with the raw bracket bodies 9 is dipped into a suitable liquid bath in which the slot 11 of every single raw bracket body 9 is trimmed by means of a wire erosion procedure. This operation may also involve several passes (for planing). The result is a very precise slot 11 with a minimal margin of error with respect to the norm.

The raw bracket body of FIG. 8 has no fixing section, because it has no slot which must be produced extremely precisely for the treatment.

After this step, the raw bracket bodies 9 of the FIGS. 6 to 8 are fixed with their slot side end in a corresponding negative form (to this end), whereas alternately a fastening is possible on the opposite end. The spacer section 9d of the respective raw bracket bodies 9 is cut through with various angles using a saw. Three parameters can be set during the cutting-through phase:

The first parameter is a distance of the resulting cut surface of the spacer section 11. The smaller this distance can be selected, the less a patient can feel the bracket.

The second parameter is an angle about the longitudinal axis of the slot 11 (mesio-distal axis). According to the deviation of the cutting angle from an average default value, the torque applied is more or less important, see FIG. 6 for nomenclature.

The third parameter is an angle with respect to a vertical line towards the longitudinal axis of the raw bracket body 9 (occlusal-gingival axis). According to the deviation of the cutting angle from an average default value, the rotation applied is more or less important, see FIG. 6 the part list.

For a raw bracket body 9, these three parameters are now established and the spacer section 9d is cut through accordingly with a saw, which enables to produce a bracket body 7. FIG. 6a shows the raw bracket body 9 of FIG. 6, at which the spacer section in terms of torque at 55° and in terms of rotation at 15° was cut through, whereby the bracket body 7 of FIG. 6a is produced. FIG. 8a shows the raw bracket body 9 of FIG. 8, at which the spacer section in terms of torque at 20° or in terms of rotation at 15° was cut through and its cut surface 10, which is arranged corresponding to these three parameters.

The bracket bodies 7 obtained in this manner are sorted into bracket body containers 25 of a bracket body library 23 (FIG. 12), wherein respectively a bracket body library is available for each raw bracket body 9 of the FIGS. 6 to 8. In other words, the raw bracket body 9 of FIG. 6 has its own bracket body library, just like that of FIGS. 7 and 8.

FIG. 12 shows a bracket body library 23, which is built analogically to the raw pad library and is filled with bracket bodies 7. The bracket bodies 7 are divided in 1° steps in terms of rotation of −5° to +5° and in terms of torque divided into 5° steps from 40° to 70°.

Naturally, other interval limits as well as other interval steps can here be used in particular also depending on the raw bracket body 9, i.e. for the raw bracket body 9 of FIG. 6 other interval limits and other interval steps can be used as for that of FIG. 7. The bracket bodies 7 along with the pad 3 form a finished bracket 1.

The method of production of a patient-specific bracket continues as follows: A patient-specific pad 3 is already fixed to the teeth in the set-up to be treated. For every pad 3, a suitable bracket body 7 is now taken from the bracket body library 23 and glued fixedly to its respective pad 3. The bracket bodies 7 are advantageously guided to the respective pad 3 via a "mechanical finger" and then glued fixedly.

A 2D-scan of the UJ and/or LJ model is taken from the bracket set-up obtained that manner from the corresponding cranial respectively caudal direction (elevation view), so as to bend a corresponding archwire using a wire bending machine using these data.

Subsequently, the plaster models are soaked in a water bath which enables to release the brackets with the bracket bodies fixedly glued thereto, which then are welded fixedly to one another using a laser.

The brackets 1 produced in that manner are placed on a plaster model of the patient (malocclusion model), see FIG. 10, and there fixed, to produce a transfer tray, for example made of silicone.

A raw pad 5 was represented respectively in FIGS. 1 to 5 for the teeth 21, 23, 27, 35 and 37. It is generally possible, to develop for every tooth of the upper and/or lower jaw respectively a raw pad 5 adapted especially to this tooth. Alternately, it is possible to use a raw pad 5 for several teeth, for instance a raw pad 5 for the teeth 32, 31, 41 and 42.

The raw pad library 19 according to FIG. 11 in each row comprises 16 raw pad containers 21, in which raw pads 5 are arranged respectively for a tooth. Consequently, raw pads 5 are respectively provided from the 8th of the one side to the 8th of the other side. The raw pad library 19 in an alternative embodiment in each row comprises 14 raw pad containers 21 in which raw pads 5 are respectively arranged for a tooth (from the 7th to the 7th). Consequently, raw pads 5 are respectively provided from the 7th of the one side to the 7th of the other side.

In the context of the present invention, by matrix-like arrangement is meant an arrangement in lines and columns.

The bracket body library 23 comprises bracket body containers 25 with bracket bodies 7 arranged therein. The bracket body containers 25 respectively the bracket bodies 7 arranged therein are hence sorted per parameter values of the three parameters (distance between cut surface and slot, angle of mesial-distal axis, angle of occlusal-gingival axis). It is generally possible to vary all three parameters in a bracket body library 23 of a bracket body 9. It is hence for instance possible again to produce the bracket body library 23 of FIG. 12 with the same values for torque and rotation, whereas however the third parameter (the distance between cut surface and slot) is varied, for instance enlarged or reduced by 1 mm. That way, there would be twice the bracket body library 23 of FIG. 12: once with a larger distance and once with a smaller distance, through which a new bracket body library 23 is built. The matrix-like arrangement of FIG. 12 is hence extended into the third dimension, in which the additional parameter is varied. This general version is in practice as a rule not necessary: Since the distance between cut surface and slot should always be as small as possible so that the generated bracket 1 disturbs the patients as little as possible, the bracket body library 23 of FIG. 12 can be sufficient, with which the distance between cut surface and slot is as small as possible.

A method for producing a patient-specific pad 3 generally comprises advantageously the following steps:

a) Providing a preferably flat section of pad material,
b) Providing a punch with at least one punching stamp for punching out at least one raw pad 5 out of the section of pad material,
c) Punching out at least one raw pad 5 out of the section of pad material using the punch, d) Production of a patient-specific set-up, in particular made of plaster, of teeth of an upper jaw and/or of a lower jaw of a patient to be treated, e) Selection of a raw pad 5 for a tooth of the patient to be treated and f) Filling a gap 27 between the raw pad 5 and the corresponding tooth in the set-up with a filling material, in particular made of plastic, to obtain a tooth-specific glued surface 3K for the pad 3, which enables a positive-locking manner with the clinical tooth of the patient.

Consequently, several raw pads 5 are advantageously punched out of the section of pad material in the step c), in particular identical or different raw pads.

A raw pad 5 is preferably punched out for all the teeth of an upper jaw and/or of a lower jaw respectively.

A pre-assembly of the at least one raw pad 5 advantageously takes place on a certain tooth after the step c), for instance in at least a following compression step, in particular a pre-assembly takes place on a respective tooth of an upper jaw and/or of a lower jaw.

The pre-assembly can include an adaptation of the buccal lingual perimeter 5U of the at least one raw pad 5, to adapt said perimeter 5U of the raw pad 5 to a certain tooth size or form.

The pre-assembly can also include a bending of selected sections of a raw pad 5, in particular the bending of mesial and/or distal sections of a raw pad 5, to build mesial and/or distal wing sections 5m, 5d of the raw pad 5 which encompass the corresponding tooth at least by sections.

The pre-assembly can moreover include a bending of an occlusal section of a raw pad 5, which then rests occlusally on the corresponding tooth.

The pre-assembly can also include the formation of lingual/buccal protrusions on at least one raw pad 5, e.g. to adapt it to a lingual concave/convex structure of a certain tooth.

In step a), a section of pad material advantageously is provided of a biocompatible metal or a biocompatible alloy, in particular titanium, gold, silver, stainless steel or a cobalt-chrome alloy.

Additionally, the raw pad 5 selected in step c) can be adapted manually to its corresponding tooth, wherein said adaptation can include an adaptation of the form and/or of the size of the raw pad.

The raw pad library 19 generally comprises in a basic variation a series of at least 14, advantageously 16, raw pad containers 21 containing respectively raw pads 5 for a tooth of an upper jaw as well as a further row of at least 14, advantageously 16, raw pad containers 21 containing respectively raw pads 5 for a tooth of a lower jaw.

The raw pad library 19 advantageously comprises for at least one tooth at least one additional raw pad container 21, in which for instance raw pads 5 of another size and/or having wing sections 5m, 5d and/or having semi-occlusal sections 5o are arranged.

The raw pad containers 21 are preferably arranged as a matrix in the raw pad library 19, in particular comparatively with a FDI dental notation.

An advantageous method for producing a patient-specific bracket having a patient-specific pad and a patient-specific bracket body can hence be split into the following steps:

1. Production of a raw pad library:
   Providing a preferably flat section of pad material,
   Providing a punch with at least one punching stamp for punching out tooth-specific raw pads out of the section of pad material,
   Punching out the tooth-specific raw pads out of the section of pad material using the punch,
   optional pre-assembly of the raw pads.

2. Production of a bracket body library:
   Providing raw bracket bodies having a spacer section,
   possibly providing highly precise slots in the raw bracket bodies (for instance with wire erosion),
   Division of the spacer sections with selected parameter values for the three parameters 3. Generating a patient-specific target set-up, in particular made of plaster, of the upper jaw and/or lower of a patient to be treated.

4. Selection of a raw pad from the raw pad library for a tooth of the patient to be treated.

5. Filling a gap between the raw pad and the corresponding tooth in the set-up with a filling material, in particular made of plastic, to obtain a tooth-specific glued surface for the pad, which enables a positive locking with the clinical tooth of the patient.

6. Selection of a bracket body from the bracket body library for each pad.

7. Fixing the bracket body on the pad, to build the patient-specific bracket.

The method steps need not however be carried out in that order. It is hence for instance possible, alternatively to first connect the raw pads 5 with their corresponding bracket bodies 7 and to build the glued surface 3K only subsequently.

LIST OF REFERENCE NUMERALS

1 bracket
3 pad
3K glued surface of the pad
5 raw pad
5m mesial (wing) section of a raw pad
5d distal (wing) section of a raw pad
5o occlusal (wing) section of a raw pad
5U buccal lingual perimeter
7 bracket body
9 raw bracket body
9d spacer section of the raw bracket body
9f fixing section of the raw bracket body
10 cut surface
11 slot
13 hook
15 wing
17 little tube
19 raw pad library
21 raw pad container
23 gracket body library
25 bracket body container
27 gap

The invention claimed is:

1. A method for producing a patient-specific bracket body (7) for a modular bracket (1) having a pad (3) and a bracket body (7), comprising:
   a) providing a raw bracket body (9) having a spacer section (9d) and a slot (11),
   b) establishing a first parameter for cutting through the spacer section (9d), a distance of a resulting cut surface of the spacer section (9d) from the slot (11), in order to establish a suitable height of the bracket body (7),
   c) establishing a second parameter for cutting through the spacer section (9d), a cutting angle to a mesio-distal axis, in order to establish a suitable torque value of the bracket body (7),
   d) establishing a third parameter for cutting through the spacer section (9d), a cutting angle to an occlusal-gingival axis, in order to establish a suitable rotation value of the bracket body (7), e) cutting through the spacer section (9*d*) according to the three established parameters, wherein said cutting creates a flat surface at the suitable height and angled at the angle to the mesio-distal axis and at the angle to the occlusal-gingival axis, whereby a bracket body (7) is produced.

2. A method according to claim 1, wherein the bracket body (9) is prepared in step a) via a MIM or a selective laser melting process and/or from a biocompatible metal or a biocompatible alloy.

3. A method according to claim 2, wherein the biocompatible metal or the biocompatible alloy is one of titanium, gold, silver, stainless steel or a cobalt-chrome alloy.

4. A method according to claim 1, wherein the cutting through in step e) comprises sawing with a saw.

5. A method according to claim 1, wherein the parameters in steps b) to d) are established individually for a given patient.

6. The method according to claim 1, wherein the parameters in steps b) to d) are respectively varied in a preset interval with preset interval steps, to generate a bracket body library (23) in which bracket bodies (7) are arranged with the respectively varied parameter values.

7. A method according to claim 1, further comprising, after steps a)-e), connecting a respective pad (3) with a respective bracket body (7) for every tooth of a patient to be treated.

8. A method according to claim 7, wherein each pad (3) is connected to the respective bracket body (7) by gluing or welding, to produce a bracket (1) for every tooth of the patient to be treated.

9. The method according to claim 8, comprising connecting the respective bracket body (7) and each pad (3) to a malocclusion model of the patient and producing a transfer tray.

\* \* \* \* \*